United States Patent
Liu et al.

(10) Patent No.: US 10,571,248 B2
(45) Date of Patent: Feb. 25, 2020

(54) TRANSPARENT FILM ERROR CORRECTION PATTERN IN WAFER GEOMETRY SYSTEM

(71) Applicant: KLA-Tencor Corporation, Milpitas, CA (US)

(72) Inventors: Helen Liu, Fremont, CA (US); Andrew Zeng, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/649,259

(22) Filed: Jul. 13, 2017

(65) Prior Publication Data

US 2018/0195855 A1 Jul. 12, 2018

Related U.S. Application Data

(60) Provisional application No. 62/443,815, filed on Jan. 9, 2017.

(51) Int. Cl.

| | |
|---|---|
| *G01B 11/06* | (2006.01) |
| *G01B 11/24* | (2006.01) |
| *G01N 21/84* | (2006.01) |
| *G01N 21/956* | (2006.01) |
| *G01N 21/95* | (2006.01) |

(52) U.S. Cl.
CPC ...... *G01B 11/0675* (2013.01); *G01B 11/2441* (2013.01); *G01N 21/8422* (2013.01); *G01N 21/9501* (2013.01); *G01N 21/956* (2013.01)

(58) Field of Classification Search
CPC . G01B 11/06; G01B 11/0616; G01B 11/0675; G01N 21/00; G01N 21/45
See application file for complete search history.

(56) References Cited

U.S. PATENT DOCUMENTS

| | | | |
|---|---|---|---|
| 5,042,949 A | 8/1991 | Greenberg et al. | |
| 6,847,458 B2 | 1/2005 | Freischlad et al. | |
| 8,068,234 B2 | 11/2011 | Tang et al. | |
| 8,803,206 B1* | 8/2014 | Or-Bach | H01L 25/0657 257/278 |
| 2007/0046953 A1* | 3/2007 | De Groot | G01B 11/0675 356/512 |
| 2010/0265516 A1 | 10/2010 | De Groot et al. | |
| 2012/0021539 A1 | 1/2012 | Allenic et al. | |

(Continued)

FOREIGN PATENT DOCUMENTS

| | | |
|---|---|---|
| JP | 2016145990 A | 8/2016 |
| JP | 2016225495 A | 12/2016 |

OTHER PUBLICATIONS

International Search Report dated Apr. 27, 2018 for PCT/US2018/012673.

*Primary Examiner* — Jonathan M Hansen
(74) *Attorney, Agent, or Firm* — Suiter Swantz pc llo

(57) ABSTRACT

A system includes one or more wafer geometry measurement tools configured to obtain geometry measurements from a wafer. The system also includes one or more processors in communication with the one or more wafer geometry measurement tools. The one or more processors are configured to apply a correction model to correct the geometry measurements obtained by the one or more wafer geometry measurement tools. The correction model is configured to correct measurement errors caused by a transparent film positioned on the wafer.

17 Claims, 11 Drawing Sheets

(56) References Cited

U.S. PATENT DOCUMENTS

| | | | |
|---|---|---|---|
| 2012/0089365 A1* | 4/2012 | Fay | G01B 11/0675 702/167 |
| 2012/0271591 A1* | 10/2012 | Kamenev | G01B 11/0675 702/167 |
| 2014/0293291 A1 | 10/2014 | Tang | |
| 2015/0043803 A1* | 2/2015 | Jeong | G06T 7/001 382/149 |

* cited by examiner

TRANSPARENT FILM ERROR CORRECTION PATTERN IN WAFER GEOMETRY SYSTEM

CROSS-REFERENCE TO RELATED APPLICATIONS

The present application claims the benefit under 35 U.S.C. § 119(e) of U.S. Provisional Application Ser. No. 62/443,815, filed Jan. 9, 2017. Said U.S. Provisional Application Ser. No. 62/443,815 is hereby incorporated by reference in its entirety.

TECHNICAL FIELD

The disclosure generally relates to the field of inspection and metrology, and particularly to inspection and metrology of semiconductor devices including transparent films.

BACKGROUND

Thin polished plates such as silicon wafers and the like are a very important part of modern technology. A wafer, for instance, may refer to a thin slice of semiconductor material used in the fabrication of integrated circuits and other devices. Other examples of thin polished plates may include magnetic disc substrates, gauge blocks, and the like. While the technique described here refers mainly to wafers, it is to be understood that the technique is also applicable to other types of polished plates as well. The term wafer and the term thin polished plate may be used interchangeably in the present disclosure.

Wafers are subjects to defect inspection as well as metrology measurements to ensure proper fabrication yield. Tools utilized to perform such inspection and metrology processes are expected to be efficient and effective. Key metrics acquired from wafers include, but are not limited to, film thickness and wafer topography. While point-to-point ellipsometer-based technologies offer sub-nanometer film thickness accuracy, full wafer optical interferometry based geometry tools may not perform well if the wafer surface contains a transparent film. For example, a pattern wafer geometry (PWG) system includes a double-sided phase shifting Fizeau interferometer and shearing interferometers. Such a PWG system may be used to simultaneously measure a wafer's front and back surfaces. However, when there are transparent films on the wafer surface, which is especially common on the front side of the wafer, the PWG measurement obtained from the wafer may contain errors due to light penetration into the film.

One solution to reduce this error is to deposit conforming/opaque film on transparent film to achieve topography measurement. This solution requires users to modify the process flow and can therefore only be applied during an engineering phase rather than in high volume production. As such, there is a desire to provide a method and system for transparent film error correction.

SUMMARY

A method is disclosed, in accordance with one or more embodiments of the present disclosure. In one embodiment, the method includes obtaining geometry measurements of a wafer utilizing a wafer geometry measurement tool. In another embodiment, the method includes applying a correction model to correct the geometry measurements obtained by the wafer geometry measurement tool, wherein the correction model is configured to correct measurement errors caused by a transparent film positioned on the wafer.

A method is disclosed, in accordance with one or more alternative embodiments of the present disclosure. In one embodiment, the method includes generating a correction model at least partially based on a design of a wafer and known physical and optical properties of a plurality of layers of the wafer. In another embodiment, the method includes obtaining geometry measurements of the wafer utilizing a wafer geometry measurement tool. In another embodiment, the method includes applying the correction model to correct the geometry measurements obtained by the wafer geometry measurement tool, wherein the correction model is configured to correct measurement errors caused by a transparent film positioned on the wafer.

A system is disclosed, in accordance with one or more alternative embodiments of the present disclosure. In one embodiment, the system includes one or more wafer geometry measurement tools configured to obtain geometry measurements of a wafer. In another embodiment, the system includes one or more processors in communication with the one or more wafer geometry measurement tools. In another embodiment, the one or more processors are configured to apply a correction model to correct the geometry measurements obtained by the one or more wafer geometry measurement tools. In another embodiment, the correction model is configured to correct measurement errors caused by a transparent film positioned on the wafer.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Embodiments of the present disclosure are directed to methods and systems for providing transparent film error corrections for optical interferometry based wafer geometry measurements systems. Such optical interferometry based wafer geometry measurement systems may include pattern wafer geometry (PWG) systems. For the purposes of the present disclosure, the terms "pattern wafer geometry" (PWG) and "optical interferometry based wafer geometry measurements systems" are used interchangeably. Phase and reflectivity change information collected from reflection on transparent film stack may be utilized to correct topography measurement errors. In some embodiments, multiple-layer stack models are utilized to estimate topography measurement errors on a three-dimensional film stack (e.g., 3D NAND film stack). The model may be configured to combine possible thickness variations of each layer and thickness gauge (e.g., reference thickness tool, such as ellipsometer) measurements at a few known locations to match an actual measured whole wafer thickness map.

Figure 1:
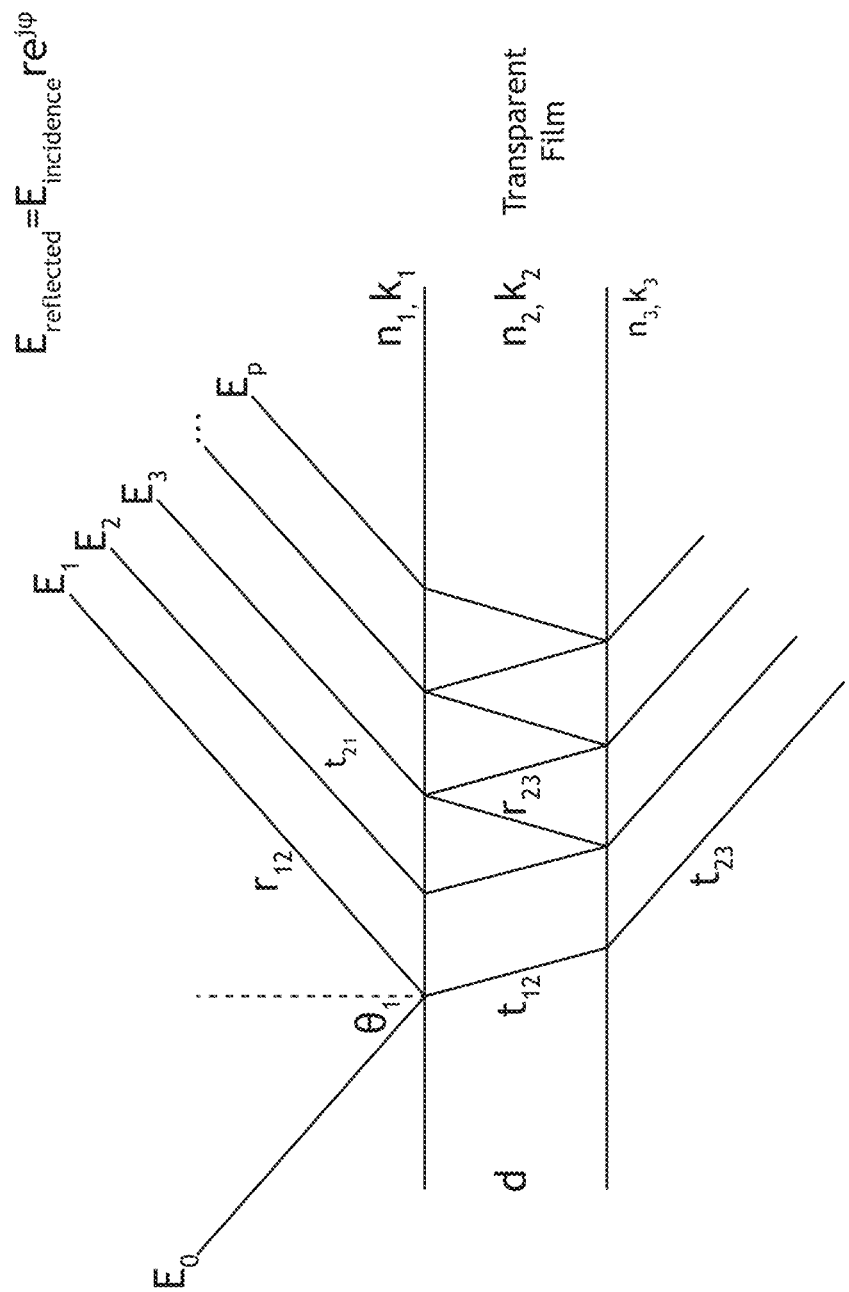
FIG. 1 is an illustration depicting transparent film errors caused by dielectric light propagation, in accordance with one or more embodiments of the present disclosure.
Figure 2:
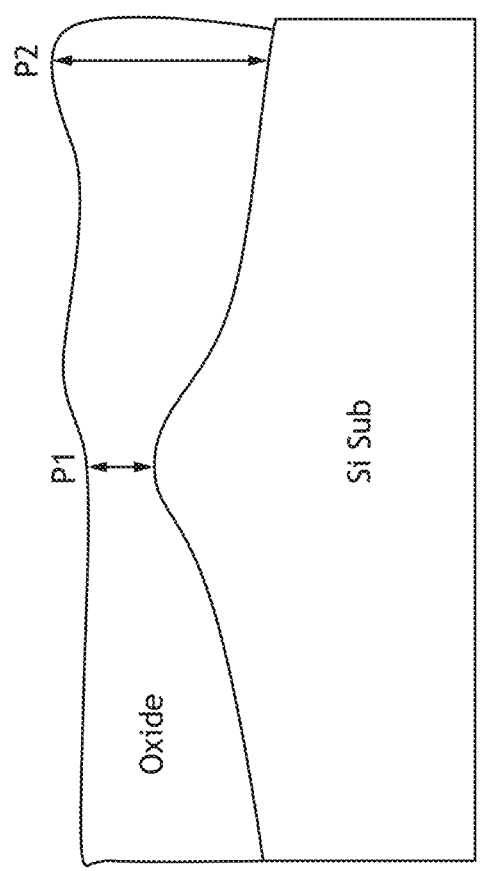
FIG. 2 is an illustration depicting a film having non-uniform thickness deposited on a wafer substrate, in accordance with one or more embodiments of the present disclosure.

Referring now to FIG. 1, an illustration depicting transparent film errors caused by dielectric light propagation is shown, in accordance with one or more embodiments of the present disclosure. It is noted that due to dielectric light propagation, the resultant overall reflection is a superimposition of multiple reflections bounced back and forth between interfaces of all underlying layers. It is also noted that the phase change ϕ due to reflection is dependent upon the layer structure of the wafer. More specifically, the phase change in the reflected beam is a function of film thickness, complex refractive index, and properties of the substrate. If the film is uniform, the phase change ϕ is constant and does not introduce topography measurement error. If the film is non-uniform, as shown on FIG. 2, the phase change ϕ will deform topography, resulting in measurement errors. In another embodiment, the reflectivity from such film stack can also be modeled as a function of the film n, k, and thickness.

Figure 3:
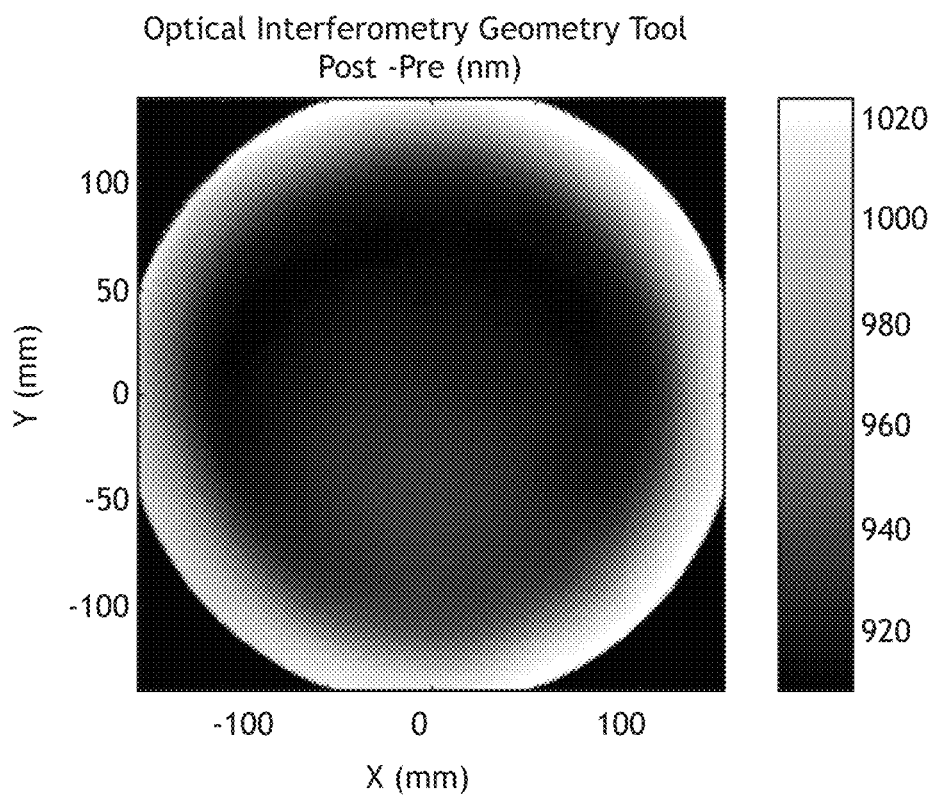
FIG. 3 is an illustration depicting a wafer thickness measurement obtained using a wafer geometry system, in accordance with one or more embodiments of the present disclosure.
Figure 4:
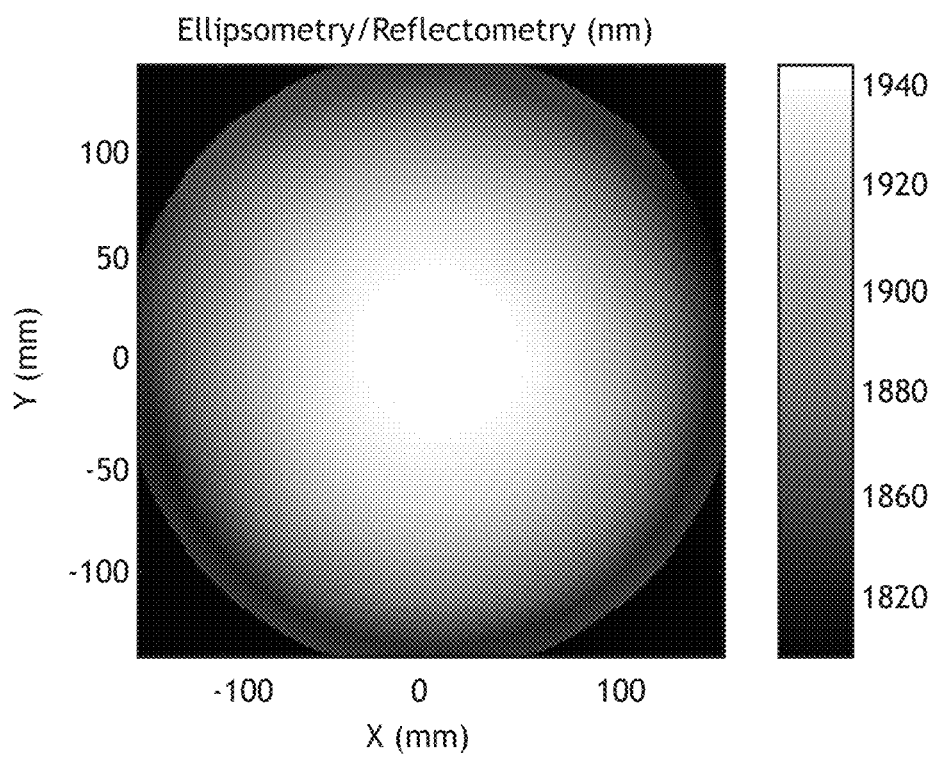
FIG. 4 is an illustration depicting a true wafer thickness measurement obtained using a reference measurement tool, in accordance with one or more embodiments of the present disclosure.
Figure 5:
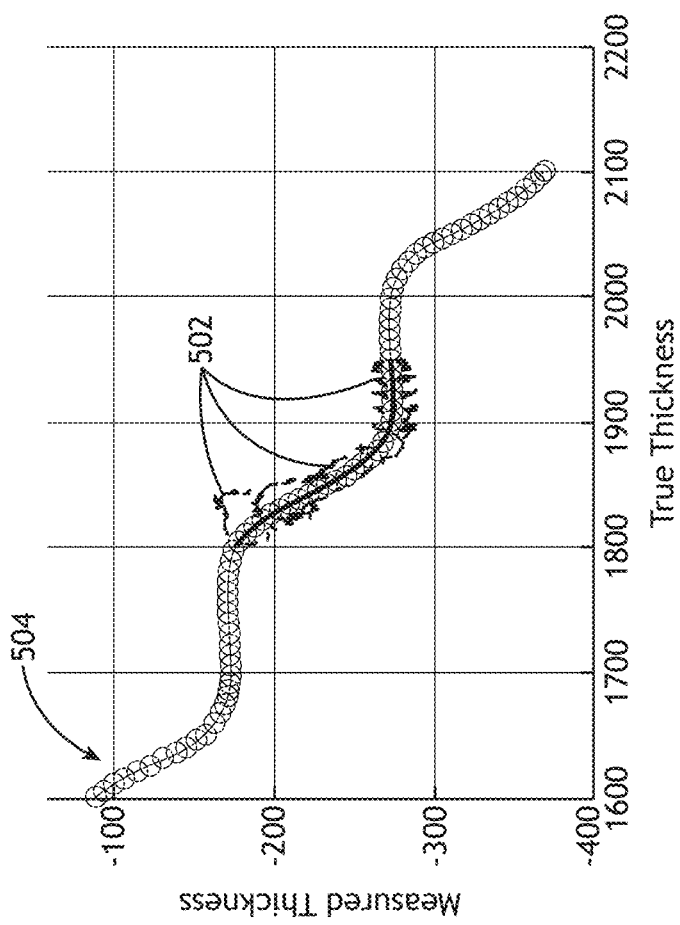
FIG. 5 is an illustration depicting a correction model configured in accordance with one or more embodiments of the present disclosure.

FIGS. 3 and 4 are illustrations depicting a type of measurement error that may be referred to as inversion error, in accordance with one or more embodiments of the present disclosure. For example, FIG. 4 shows a true film thickness of a wafer, which has a film of the center region thicker than the film of the edge region. It is contemplated that various types of measurement tools may be utilized to assist in measuring the true film thickness. For example, broadband ellipsometry film tools, on-tool broadband reflectometer thickness probes, capacitance gauges, optical thickness gauges, or the like may be utilized without departing from the spirit and scope of the present disclosure. FIG. 3, on the other hand, shows the wafer thickness measured using interferometry data (e.g., measured using a PWG measurement tool) without transparent film error correction. It is noted that the wafer thickness measured using optical interferometry data is the opposite of the true thickness due to inversion error of the transparent film. This relationship is illustrated in FIG. 5.

It is contemplated that the quantitative relationship between the true thickness and the PWG measured thickness can be modeled through the optical characteristics of the film. In some embodiments, the correction model may include a correction curve, as illustrated in FIG. 5. For instance, the correction curve 504 may be generated from simulation. In FIG. 5, the x-axis indicates true thickness, measured in nanometers (nm), which is determined via a point-to-point thickness measurement reference. The y-axis displays the measured, or apparent, thickness, which includes the error induced by the transparent film and is measured via an optical interferometer. Experimental data 502, representing both true thickness and PWG measured thickness, may be collected to verify the correction curve 504. Once the correction curve 504 is obtained, subsequent PWG measured thickness may be corrected using the correction curve 504 to produce thickness measurements that closely resemble the true thickness.

Figure 6:
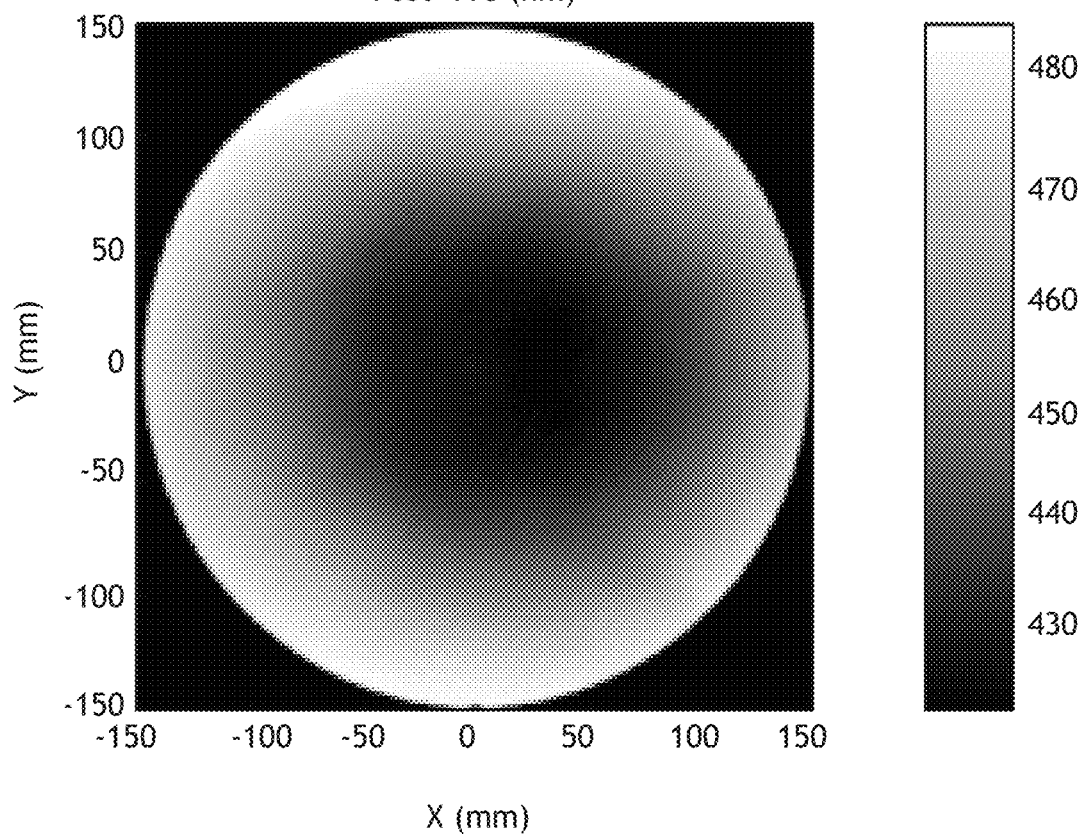
FIG. 6 is an illustration depicting another wafer thickness measurement obtained using a wafer geometry system, in accordance with one or more embodiments of the present disclosure.
Figure 7:
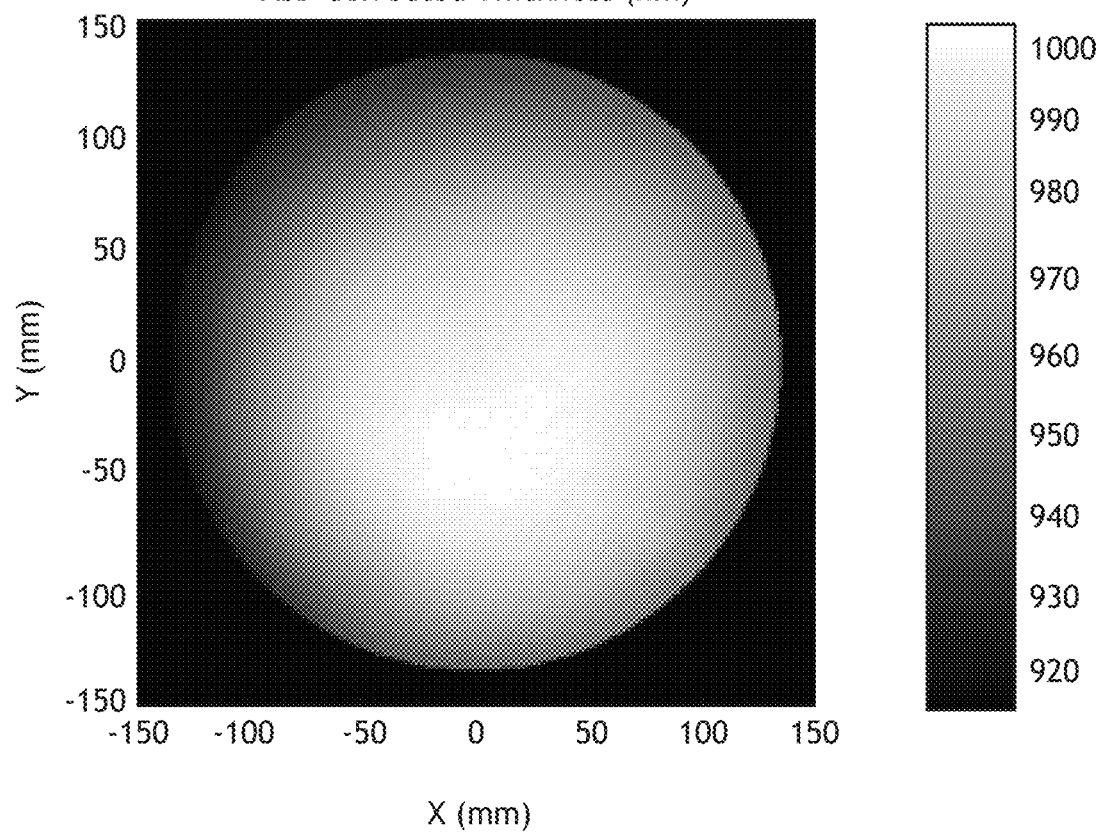
FIG. 7 is an illustration depicting a wafer thickness measurement corrected utilizing a correction model, in accordance with one or more embodiments of the present disclosure.
Figure 8:
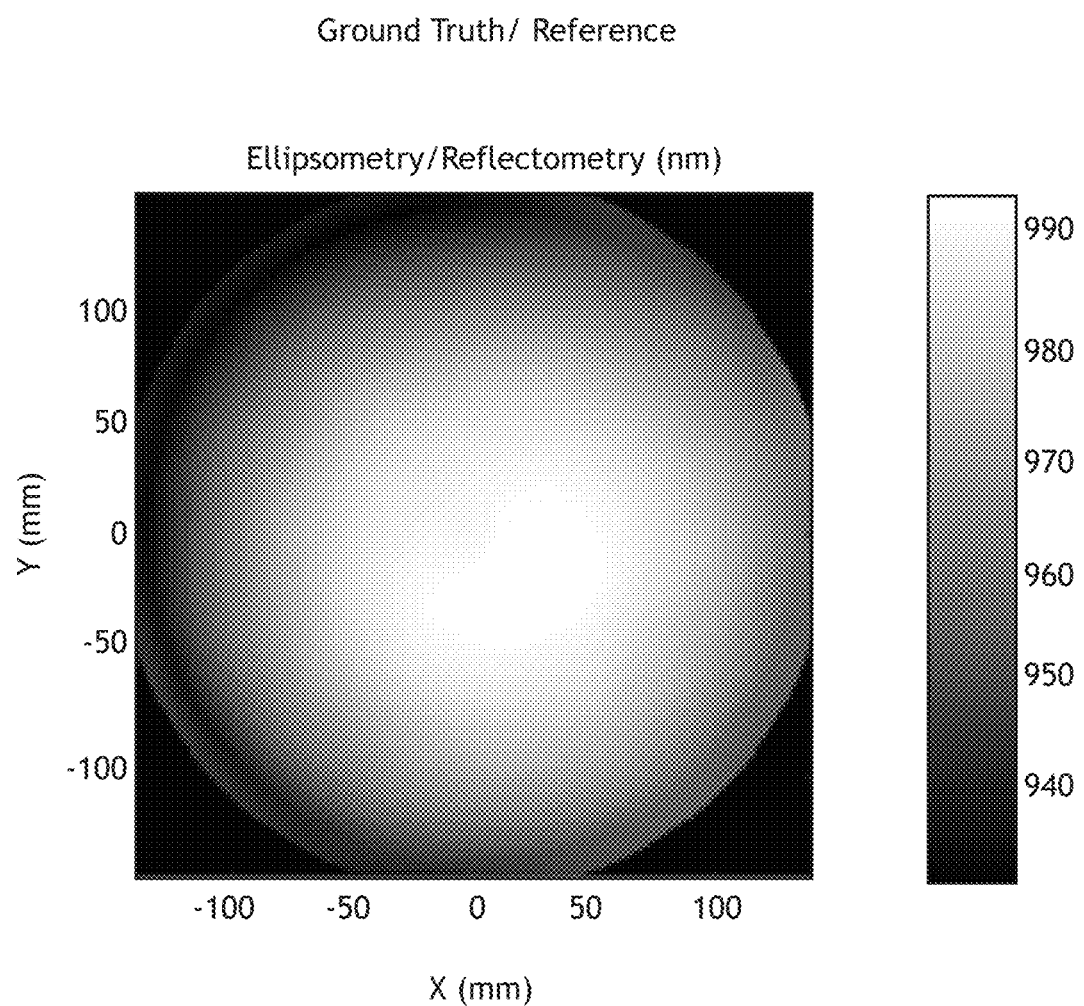
FIG. 8 is an illustration depicting a true wafer thickness measurement as a reference for the wafer thickness measurement corrected utilizing a correction model, in accordance with one or more embodiments of the present disclosure.

This correction process is further illustrated in FIGS. 6-8. FIG. 6 is a depiction of PWG measurement obtained before correction. The PWG measurement may then be corrected by applying a correction curve to it. The resulting measurement may be referred to as the corrected PWG measurement, which is shown in FIG. 7. It is noted that the corrected PWG measurement may accurately reflect the true thickness data, which is represented in FIG. 8. With such a correction method, the correlation between a corrected PWG thickness measurement and a reference tool (e.g., ellipsometer) thickness measurement may approach 97%.

Figure 9A:
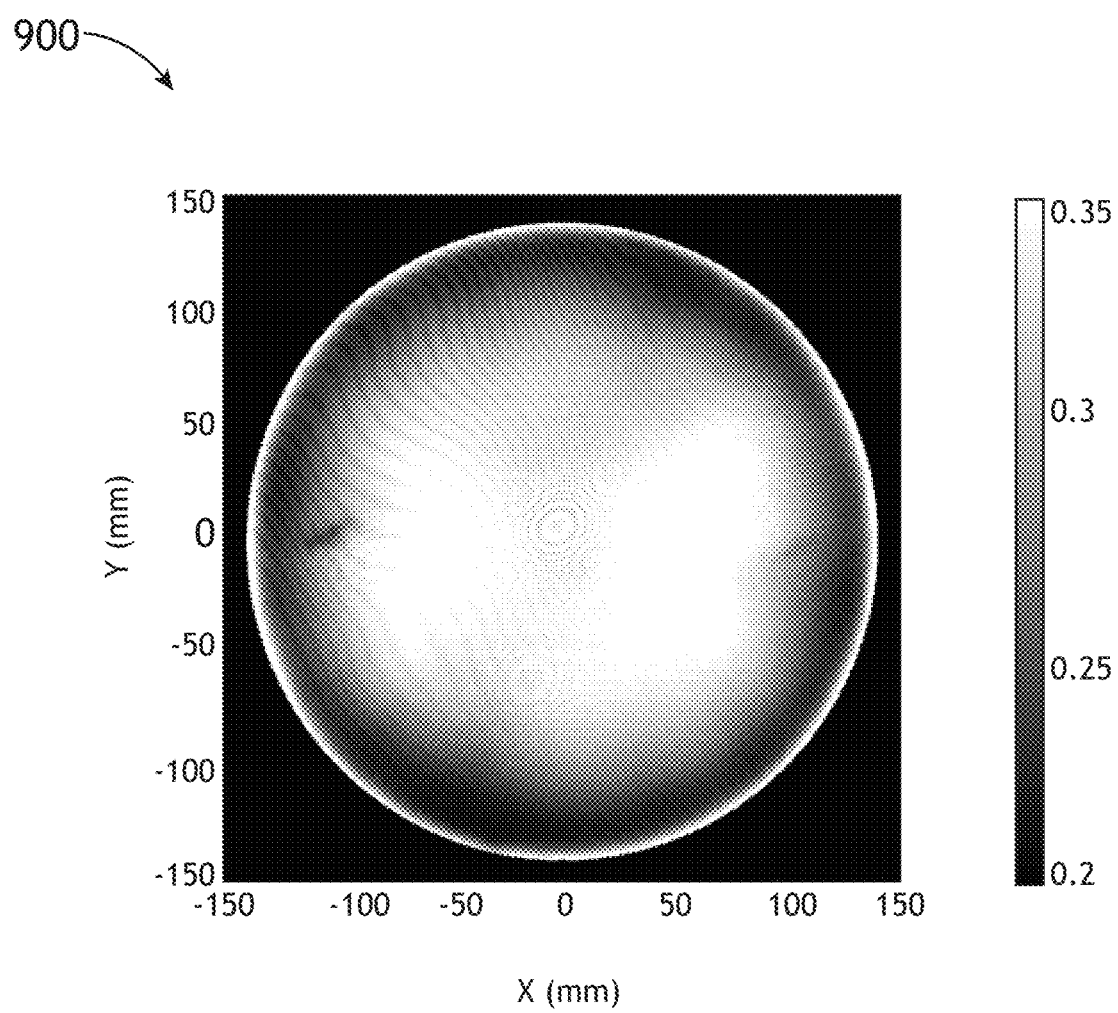
FIGS. 9A-9B illustrate reflectivity information obtained from a film stack, in accordance with one or more embodiments of the present disclosure.
Figure 9B:
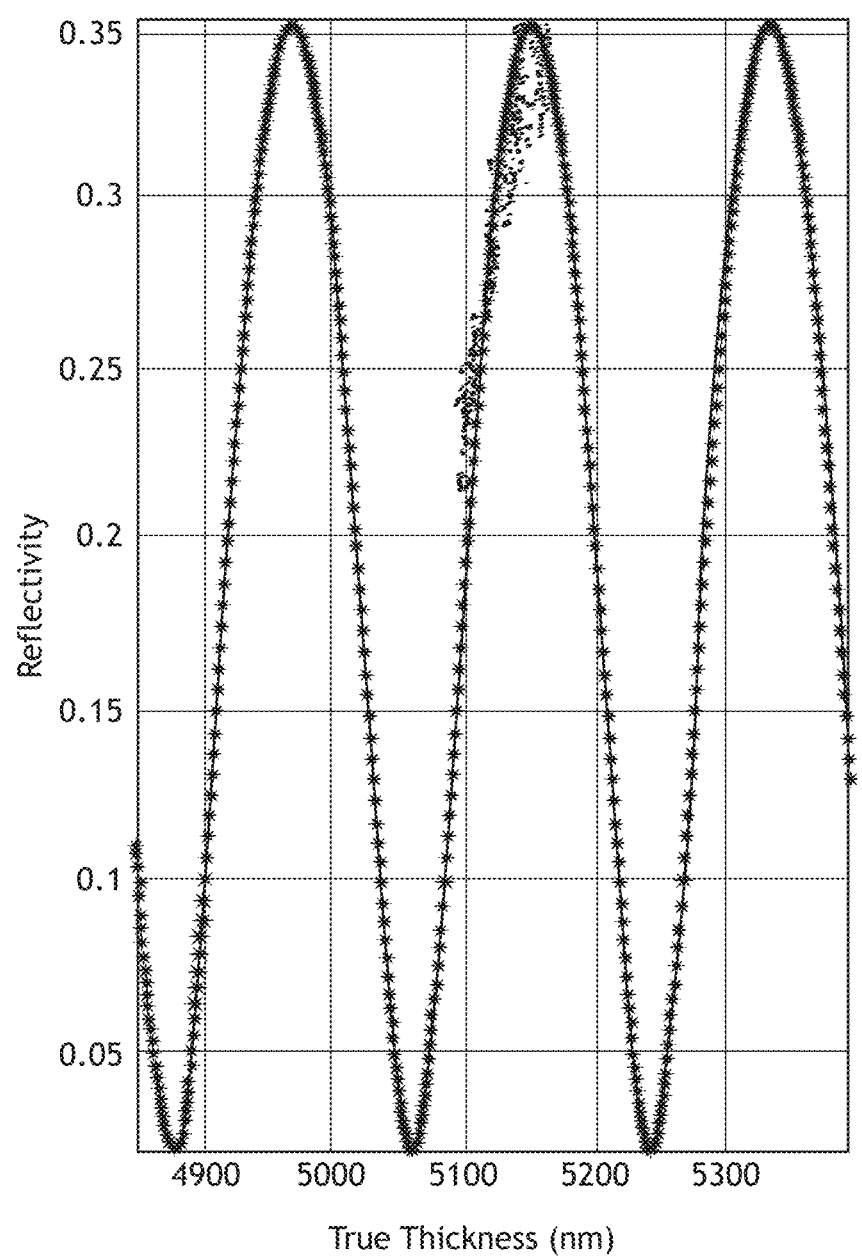

It is contemplated that the correction process described above may be further assisted with the utilization of reflectivity information, r, and phase data, φ, which is used directly for thickness measurements, as noted in the relationship: $\vec{E}_{reflected} = \vec{E}_{incidence} r e^{j\varphi}$, which originates from the same interferometer intensity data as used above. In some embodiments, a single wavelength interferometer may be used to collect spatial information from multiple wafer surface locations. The information collected may then be processed to generate a wafer map with reflectivity information, which may be utilized to further improve the accuracy of the corrected PWG measurement. FIGS. 9A and 9B illustrate reflectivity information obtained from a film stack. FIG. 9A illustrates reflectivity measured across a sample using a PWG system. FIG. 9B illustrates the similarity between the measured reflectivity and the modeled reflectivity with respect to the film thickness change. It is noted that because only interferometry information post-film deposition is used for reflectivity measurement, this process may be accomplished in a single process step, which is more efficient than using two steps to measure surface topography before/after film deposition/etching to derive film thickness.

It is also contemplated that the correction process described above may be configured to accommodate larger thickness ranges without departing from the spirit and scope of the present disclosure. For example, phase unwrapping techniques may be applied to the correction curve described above to extend its thickness coverage to match a specific need. The correction process described above may be carried out by, but not limited to, one or more of the following algorithms: a fitting of interferometer intensity data, reflectivity, phase error vs. model result, a set of denoising/filtering techniques, a prediction algorithm, a statistical optimization algorithm, and a neural network algorithm with input from interferometer.

Figure 10:
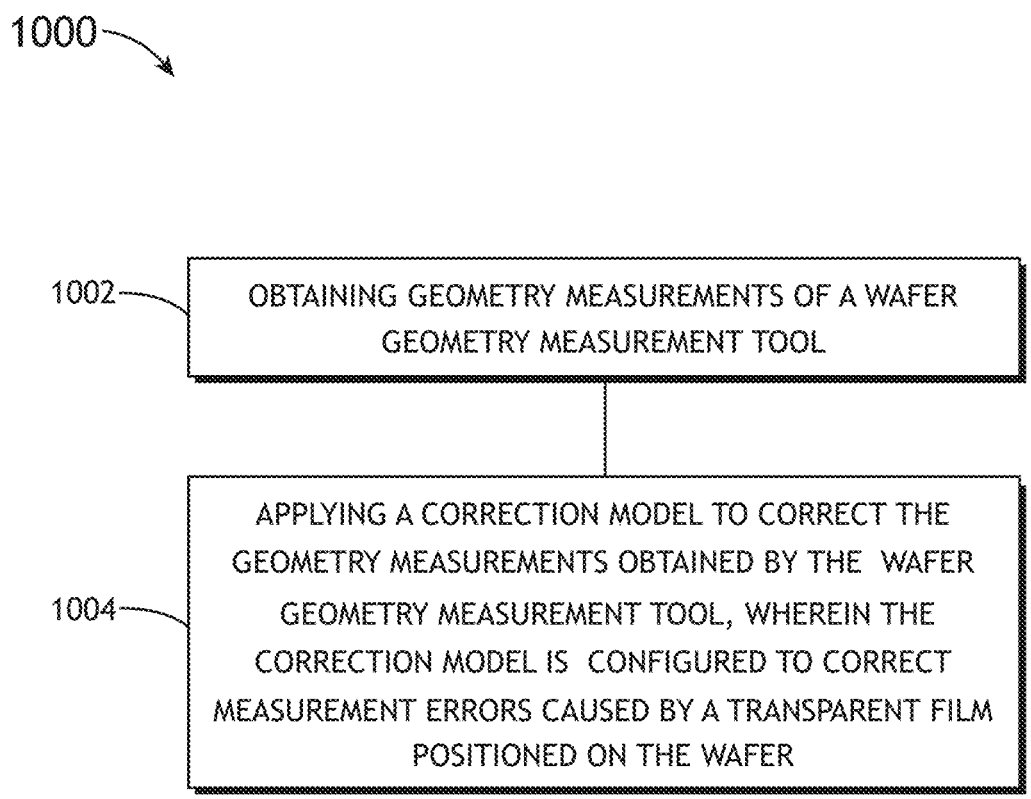
FIG. 10 is a flow diagram depicting a wafer measurement correction method, in accordance with one or more embodiments of the present disclosure.

FIG. 10 is a flow diagram depicting an embodiment of a correction process 1000 configured in accordance with the present disclosure. As shown in FIG. 10, a wafer geometry system is utilized to obtain geometry measurements of a wafer in a step 1002. The geometry measurements obtained may include errors such as topography measurement errors and the like caused by transparent films positioned on the wafer. A correction model may then be utilized to help reduce the errors obtained in the geometry measurements in a step 1004. As previously described, the correction model may help correct measurement errors caused by the transparent films positioned on the wafer. In some embodiments, the correction model may be obtained a priori based on the correlation between true wafer thickness and measured wafer thickness data. In some embodiments, the correction model may involve the use of a correction curve as previously described. In other embodiments, the correction model may involve the use of both the a priori method and the correction curve method described above.

It is contemplated that the correction model may be dynamically updated in some embodiments. For instance, the output of step 1004 may be examined against some reference data to determine the effectiveness of the correction model. In some embodiments, a feedback loop may be provided to adjust the correction model if doing so can further reduce measurement errors. In some embodiments, the correction model may be generated based on the design of the wafer and known physical (and optical) properties of the various layers of the wafer. It is contemplated that various other types of techniques may be utilized to help generate/update the correction model without departing from the spirit and scope of the present disclosure.

Figure 11:
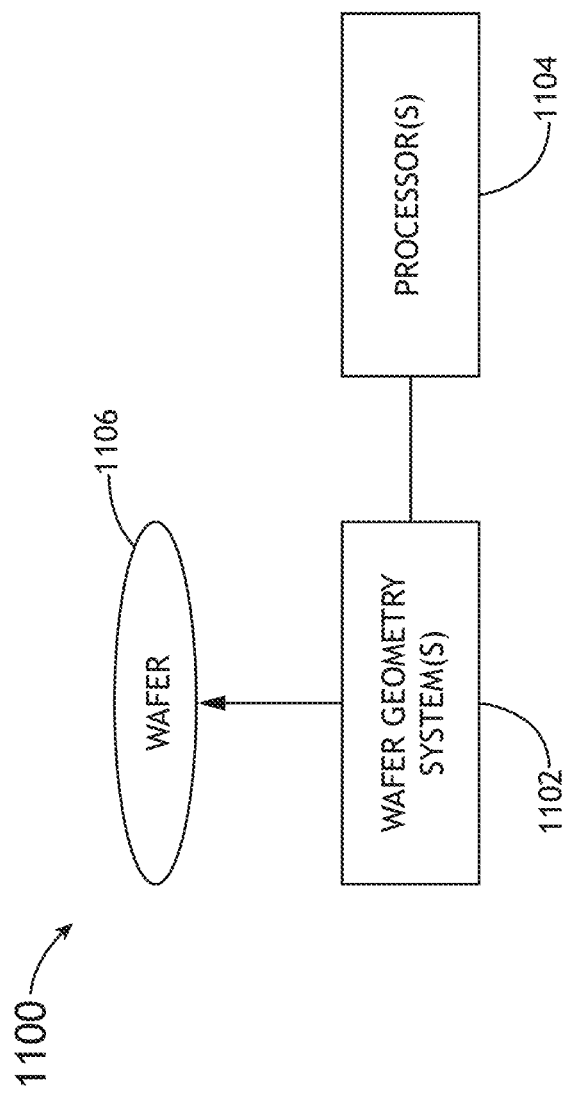
FIG. 11 is a block diagram depicting an inspection system configured in accordance with one or more embodiments of the present disclosure.

Referring now to FIG. 11, a block diagram depicting an inspection system 1100 configured in accordance with one or more embodiments of the present disclosure is shown. In one embodiment, the inspection system 1100 includes one or more wafer geometry tools 1102. The wafer geometry tool 1102 may be configured to obtain wafer geometry measurements from wafer 1106. For example, the wafer geometry tool 1102 may include, but is not limited to, a dual cavity Fizeau interferometer. A description of a dual interferometer suitable for implementation in one or more embodiments of the present disclosure is provided in U.S. Pat. No. 6,847,458, issued on Jan. 25, 2005, which is incorporated herein by reference in the entirety. A description of a dual interferometer suitable for implementation in one or more embodiments of the present disclosure is provided in U.S. Pat. No. 8,068,234, issued on Nov. 29, 2011, which is incorporated herein by reference in the entirety. A description of a dual interferometer suitable for implementation in one or more embodiments of the present disclosure is provided in U.S. Patent Publication No. 2014/0293291, published on Oct. 2, 2014, which is incorporated herein by reference in the entirety.

In another embodiment, the inspection system 1100 includes one or more processors 1104 (e.g., one or more computer processors). The one or more processors 1104 may be communicatively coupled to the wafer geometry tool 1102 and configured to receive one or more measurements from the wafer geometry tool 1102. In one embodiment, the one or more processors 1104 may be embodied in a controller. The processors 1104 may be configured to apply a correction model to the wafer geometry measurements obtained. The correction model may be obtained a priori. The correction model may also be dynamically adjustable as described above.

As will be appreciated from the above, the correction system and process described above enable accurate measurement of thick opaque film deposited on transparent film stacks, which is a key potential application in 3D NAND production. The correction system and process described above will significantly reduce transparent film induced topography measurement error without adding opaque film to fabrication process. Based on the corrected topography measurements, the system 1100 may be used to provide feedback and/or feedforward control in order to adjust upstream or downstream process tools in the semiconductor fabrication facility (e.g., 3D NAND facility).

The one or more processors 1104 may include any one or more processing elements known in the art. It is to be understood that each of the processor(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If a computer system includes more than one computer subsystems, then the different computer subsystems may be coupled to each other such that images, data, information, instructions, etc. can be sent between the computer subsystems as described further herein. For example, one computer subsystem may be coupled to additional computer subsystem(s) by any suitable transmission media, which may include any suitable wired and/or wireless transmission media known in the art. Two or more of such computer subsystems may also be effectively coupled by a shared computer-readable storage medium. In general, the term "processor" may be broadly defined to encompass any device having one or more processing elements, which execute program instructions from a non-transitory memory medium (i.e., memory). Moreover, different subsystems of the system 1100 (e.g., wafer geometry tool 1102, user interface, and the like) may include processor or logic elements suitable for carrying out at least a portion of the steps described throughout the present disclosure.

It is contemplated that an additional embodiment of the present disclosure relates to a non-transitory computer-readable medium storing program instructions executable on a computer system for performing a computer-implemented method for target placement as described above. The computer-readable medium may be a storage medium such as a magnetic or optical disk, a magnetic tape, or any other suitable non-transitory computer-readable medium known in the art. The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension), or other technologies or methodologies, as desired.

It is also to be understood that while the examples above referred to wafers, the systems and methods in accordance with the present disclosure are applicable to other types of polished plates as well without departing from the spirit and scope of the present disclosure. The term wafer used in the present disclosure may include a thin slice of semiconductor material used in the fabrication of integrated circuits and other devices, as well as other thin polished plates such as magnetic disc substrates, gauge blocks, and the like.

It is contemplated that the methods and systems described in the present disclosure may be implemented as standalone products or as components of various wafer measurement, inspection, and/or hotspot discovery tools. It is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. It is also understood that the various blocks depicted in the figures are presented separately for illustrative purposes. It is contemplated that while the various blocks depicted in the figures may be implemented as separate (and communicatively coupled) devices and/or processing units, they may also be integrated together without departing from the spirit and the scope of the present disclosure.

All of the methods described herein may include storing results of one or more steps of the method embodiments in a memory medium. The results may include any of the results described herein and may be stored in any manner known in the art. The memory medium may include any memory medium described herein or any other suitable memory medium known in the art. After the results have been stored, the results can be accessed in the memory medium and used by any of the method or system embodiments described herein, formatted for display to a user, used by another software module, method, or system, etc. Furthermore, the results may be stored "permanently," "semi-permanently," temporarily," or for some period of time. For example, the memory medium may be random access memory (RAM), and the results may not necessarily persist indefinitely in the memory medium.

It is further contemplated that each of the embodiments of the method described above may include any other step(s) of any other method(s) described herein. In addition, each of the embodiments of the method described above may be performed by any of the systems described herein.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, applications programs, one or more interaction devices, such as a touch pad or screen, and/or control systems including feedback loops and control motors (e.g., feedback for sensing position and/or velocity, and control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable and/or wirelessly interacting components, and/or logically interacting and/or logically interactable components.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

What is claimed is:

1. A wafer geometry measurement method comprising:
    obtaining geometry measurements of a three-dimensional NAND structure utilizing a wafer geometry measurement tool; and
    applying, with one or more processors, a multi-layer stack correction model to correct the geometry measurements obtained by the wafer geometry measurement tool from the three-dimensional NAND structure, wherein the multi-layer stack correction model includes a simulated correction curve representing a correlation between a true thickness and a measured thickness, wherein the multi-layer stack correction model is configured to correct one or more measurement errors in topographical data caused by a transparent film positioned on the three-dimensional NAND structure based on reflectivity and phase change information measured from the transparent film; and
    providing one or more control signals to one or more process tools in a semiconductor fabrication facility based on the corrected geometry measurements.

2. The method of claim 1, wherein the correction model is obtained at least partially based on correlations between true wafer thickness data and wafer thickness data measured using the wafer geometry measurement tool.

3. The method of claim 1, wherein the correction model is obtained at least partially based on a design of the wafer and known physical and optical properties of a plurality of layers of the wafer.

4. The method of claim 1, wherein the correction model further takes into account a wafer map with reflectivity information.

5. The method of claim 4, wherein the wafer map with reflectivity information is obtained utilizing a single wavelength interferometer that collects spatial information from multiple wafer surface locations.

6. The method of claim 1, wherein the correction curve supports wrapping and unwrapping.

7. A wafer geometry measurement method comprising:
    generating a multi-layer stack correction model at least partially based on a design of a wafer and known physical and optical properties of a three-dimensional NAND structure of the wafer, wherein the multi-layer stack correction model includes a simulated correction curve representing a correlation between a true thickness and a measured thickness;
    obtaining geometry measurements of the wafer utilizing a wafer geometry measurement tool;
    applying the correction model to correct the geometry measurements obtained by the wafer geometry measurement tool, wherein the correction model is configured to correct measurement errors in topographical data caused by a transparent film positioned on the three-dimensional NAND structure of the wafer; and
    providing one or more control signals to one or more process tools in a semiconductor fabrication facility based on the corrected geometry measurements.

8. The method of claim 7, wherein the correction model is generated at least partially based on correlations between true wafer thickness data and wafer thickness data measured using the wafer geometry measurement tool.

9. The method of claim 7, wherein the correction model further takes into account for a wafer map with reflectivity information.

10. The method of claim 9, wherein the wafer map with reflectivity information is obtained utilizing a single wavelength interferometer that collects spatial information from multiple wafer surface locations.

11. The method of claim 7, wherein the correction curve supports wrapping and unwrapping.

12. A system comprising:
    one or more wafer geometry measurement tools configured to obtain geometry measurements of a three-dimensional NAND structure of a wafer; and
    one or more processors in communication with the one or more wafer geometry measurement tools, the one or more processors configured to:
    apply a multi-layer stack correction model to correct the geometry measurements obtained by the wafer geometry measurement tool from the three-dimensional NAND structure, wherein the multi-layer stack correction model includes a simulated correction curve representing a correlation between a true thickness and a measured thickness, wherein the multi-layer stack correction model is configured to correct one or more measurement errors in topographical data caused by a transparent film positioned on the three-dimensional NAND structure based on reflectivity and phase change information measured from the transparent film; and
    provide one or more control signals to one or more process tools in a semiconductor fabrication facility based on the corrected geometry measurements.

13. The system of claim 12, wherein the correction model is obtained at least partially based on correlations between true wafer thickness data and wafer thickness data measured using the wafer geometry measurement tool.

14. The system of claim 12, wherein the correction model is obtained at least partially based on a design of the wafer and known physical and optical properties of a plurality of layers of the wafer.

15. The system of claim 12, wherein the correction model further takes into account for a wafer map with reflectivity information.

16. The system of claim 15, wherein the wafer map with reflectivity information is obtained utilizing a single wavelength interferometer that collects spatial information from multiple wafer surface locations.

17. The method of claim 12, wherein the correction curve supports wrapping and unwrapping.

* * * * *